United States Patent
Ein-Gal

(10) Patent No.: US 7,489,764 B2
(45) Date of Patent: Feb. 10, 2009

(54) ADJUSTABLE APERTURE COLLIMATOR

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 2 days.

(21) Appl. No.: 11/772,326

(22) Filed: Jul. 2, 2007

(65) Prior Publication Data

US 2009/0010395 A1   Jan. 8, 2009

(51) Int. Cl.
*G21K 1/04* (2006.01)

(52) U.S. Cl. .......................... 378/150; 378/65; 378/151

(58) Field of Classification Search ............ 378/65, 378/150, 151
See application file for complete search history.

(56) References Cited

U.S. PATENT DOCUMENTS

| | | | | |
|---|---|---|---|---|
| 3,755,672 A | * | 8/1973 | Edholm et al. | 378/158 |
| 4,856,042 A | * | 8/1989 | Staron et al. | 378/147 |
| 5,148,465 A | * | 9/1992 | Mulder et al. | 378/156 |
| 6,920,203 B2 | * | 7/2005 | Short et al. | 378/147 |
| 7,082,189 B2 | * | 7/2006 | Yahata et al. | 378/156 |
| 7,209,547 B2 | * | 4/2007 | Baier et al. | 378/149 |
| 7,308,073 B2 | * | 12/2007 | Tkaczyk et al. | 378/16 |

\* cited by examiner

*Primary Examiner*—Edward J Glick
*Assistant Examiner*—Thomas R Artman
(74) *Attorney, Agent, or Firm*—Dekel Patent Ltd.; David Klein

(57) ABSTRACT

A collimator including an inner border whose inner perimeter defines an aperture, an outer border positioned outwards of the inner border, an enclosure being defined and bounded between the inner and outer borders, the enclosure being sufficiently filled with a radiopaque pliable material so as to block a predefined amount of radiation from passing through the enclosure, while allowing radiation to pass through the aperture, and at least one actuator attached to at least one point of the inner border operable to deform the inner border so as to modify a shape of the aperture.

9 Claims, 2 Drawing Sheets

ADJUSTABLE APERTURE COLLIMATOR

FIELD OF THE INVENTION

The present invention relates generally to radiotherapy and irradiation systems, and particularly to an adjustable aperture collimator useful in such radiotherapy and irradiation systems.

BACKGROUND OF THE INVENTION

Multi-leaf collimators (MLCs) are used in radiotherapy for aperture forming intended to shape a radiation beam. Examples of multiple layer MLCs include those described in U.S. Pat. Nos. 6,266,393 and 6,526,123 and to Ein-Gal, the disclosures of which are incorporated herein by reference. MLCs provide a stationary aperture for radiotherapy.

Dynamic aperture formation is also known in the art. For example, U.S. Pat. No. 4,868,843 to Nunan describes a system that dynamically controls an x-ray field of a fan beam. A multileaf collimator is positioned in the fan beam including a first set of leaves which can be individually moved into or out of the fan x-ray beam to block or pass individual radiation pixels. Continuous monitoring of alignment of the patient's anatomy with both inner and outer edges of the fan beam is obtained with a linear detector array retractably mounted on the opposite side of the patient from the x-ray source. Tapered extensions, added to a second opposite set of leaves of the MLC are variably positionable to attenuate the dose rate in individual radiation pixels of the fan x-ray beam. The patient scan is obtained by moving the patient perpendicularly to and through the fan x-ray field while the dose delivered in each radiation pixel is dynamically controlled. Normal tissue is protected by the positions of the first set of leaves of the MLC, which attenuate transmission to less than 5% of open field dose. Depth variations from the patient surface to the plane at treatment depth are compensated at each radiation pixel of the field by the positions of the tapered extensions of the second, opposite, set of leaves of the MLC, providing variable transmission from 50% to 100% of open field dose, for example. Reduced dose to critical organs such as the spinal cord can thereby be delivered in each treatment fraction However, dynamic aperture formation for target tracking requires leaf speed significantly higher than presently available. Increasing MLC leaf speed is presently complicated and expensive.

SUMMARY OF THE INVENTION

The present invention seeks to provide a novel device and method for aperture formation for MLCs, which can provide fast aperture motion, as is described hereinbelow.

There is thus provided in accordance with an embodiment of the present invention a collimator including an inner border whose inner perimeter defines an aperture, an outer border positioned outwards of the inner border, an enclosure being defined and bounded between the inner and outer borders, the enclosure being sufficiently filled with a radiopaque pliable material so as to block a predefined amount of radiation from passing through the enclosure, while allowing radiation to pass through the aperture, and at least one actuator attached to at least one point of the inner border operable to deform the inner border so as to modify a shape of the aperture.

The radiopaque pliable material may include a radiopaque liquid, a radiopaque powder, a dispersion (e.g., suspension or emulsion) of powdered radiopaque material in a carrier or a radiopaque gas.

The inner border may be constructed of a flexible material, such as rubber.

A sensor may be provided that senses a parameter related to irradiation. The sensor is in operative communication with the at least one actuator, and the at least one actuator changes the shape of the aperture in accordance with information sensed by the sensor.

The collimator may further include apparatus for determining position and shape of the aperture (e.g., a camera).

There is also provided in accordance with an embodiment of the present invention an irradiation system including a source of radiation that emits a radiation beam, and a collimator that collimates the radiation beam, the collimator including an inner border whose inner perimeter defines an aperture, an outer border positioned outwards of the inner border, an enclosure being defined and bounded between the inner and outer borders, the enclosure being sufficiently filled with a radiopaque pliable material so as to block a predefined amount of radiation from passing through the enclosure, while allowing radiation to pass through the aperture, and at least one actuator attached to at least one point of the inner border operable to deform the inner border so as to modify a shape of the aperture.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
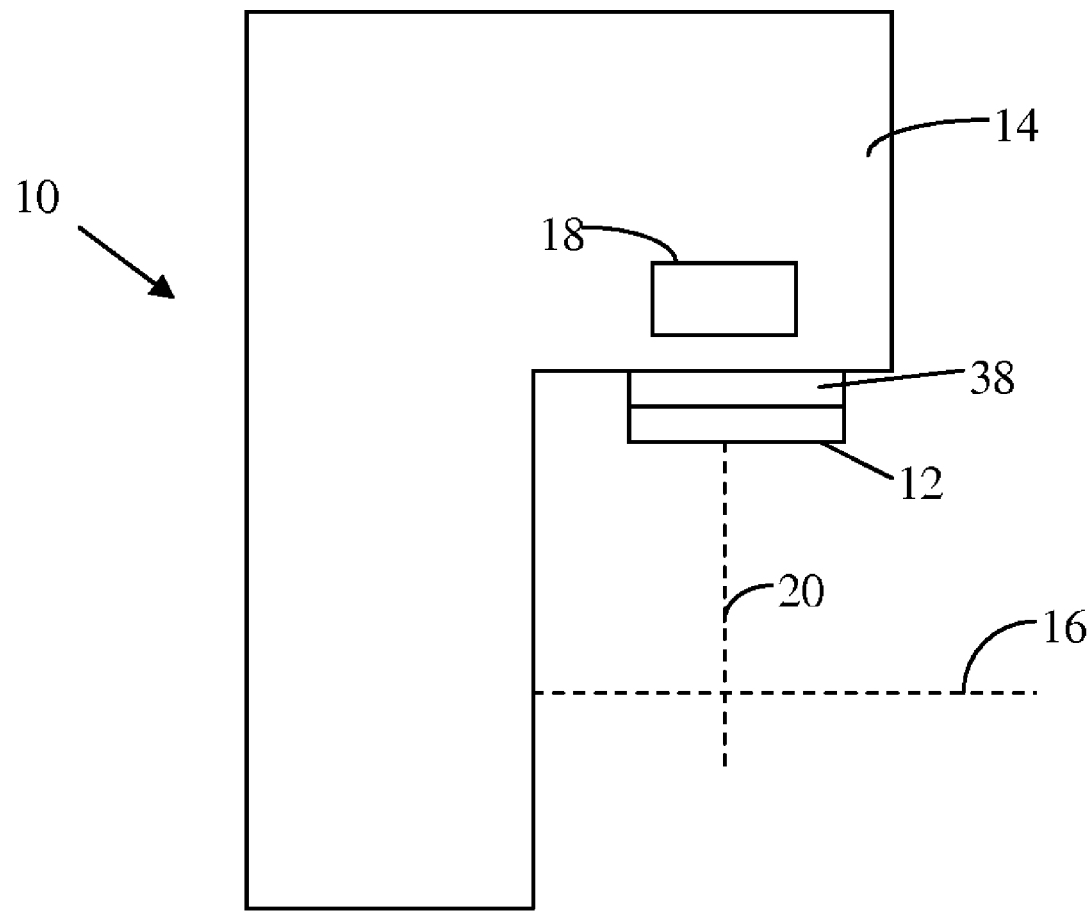
FIG. 1 is a simplified pictorial illustration of an irradiation system with an adjustable aperture collimator, constructed and operative in accordance with an embodiment of the present invention.

Reference is now made to FIG. 1, which illustrates an irradiation system 10 with an adjustable aperture collimator 12, constructed and operative in accordance with an embodiment of the present invention.

In the non-limiting illustrated embodiment, irradiation system 10 (e.g., a LINAC) includes a gantry 14 which can be rotated about a horizontal axis 16 in the course of a therapeutic treatment. Collimator 12 is fastened to an extension of gantry 14 in which is disposed a source 18 of radiation, such as a linear accelerator, for generating a radiation beam 20. Any radiation may be used, such as but not limited to, electron radiation or photon radiation (gamma radiation). As is known in the art, during treatment, beam 20 is trained on a target which lies in the isocenter of the gantry rotation. Imaging apparatus (not shown), such as a fluoroscope or ultrasound apparatus, for example, may be provided for imaging the target irradiated by radiation beam 20. The imaging apparatus may be used in conjunction with a closed loop, feedback control system (not shown) for controlling a position of gantry 14 and for controlling the functioning of collimator 12.

Figure 2:
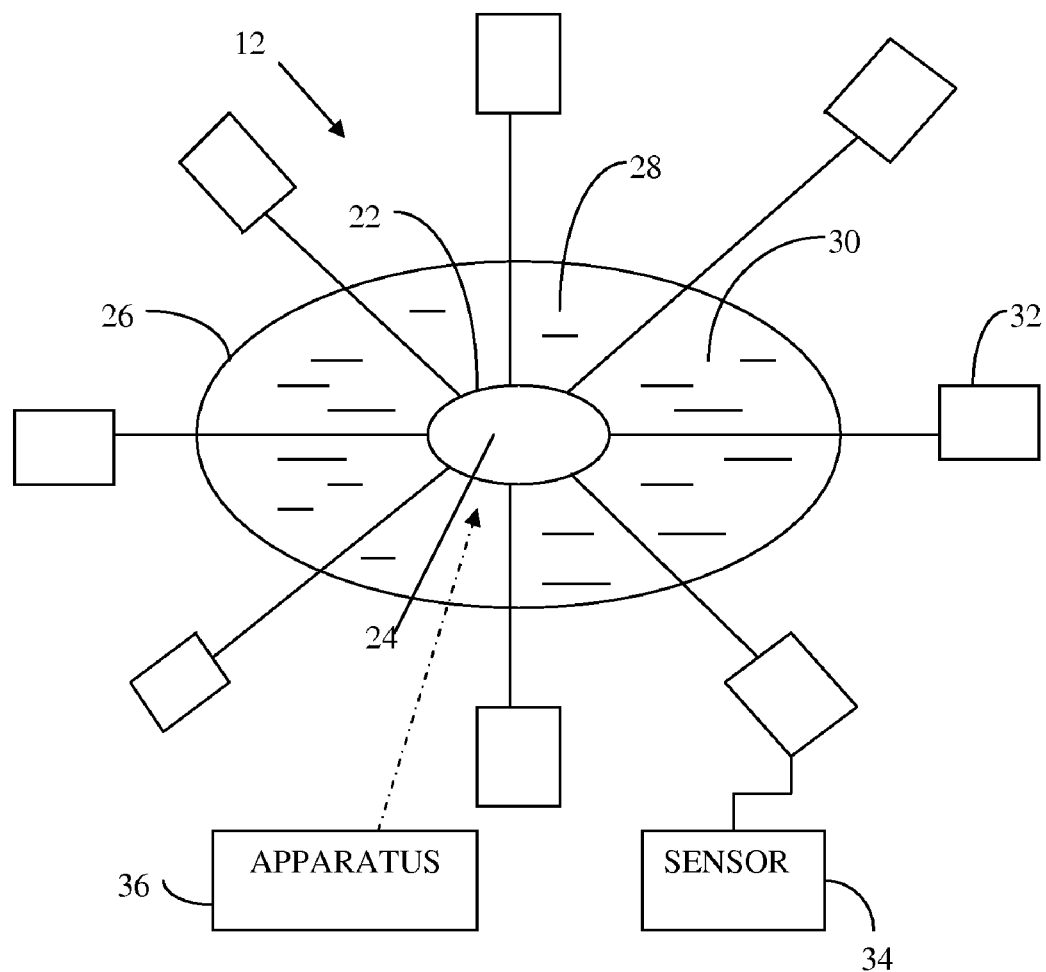
FIG. 2 is a simplified pictorial illustration of the adjustable aperture collimator of FIG. 1, constructed and operative in accordance with an embodiment of the present invention.

Reference is now made to FIG. 2, which illustrates the adjustable aperture collimator 12 of FIG. 1, in accordance with a non-limiting embodiment of the present invention.

Collimator 12 includes an inner border 22 (of any arbitrary shape) whose inner perimeter defines an aperture 24 (of any arbitrary shape). The inner border 22 may be constructed of a flexible material, such as rubber. An outer border 26 (of any arbitrary shape) is positioned outwards of the inner border 22.

The outer border 26 may be constructed of a flexible material, such as rubber, or of a rigid material, such as metal. An enclosure 28 is defined and bounded between the inner and outer borders 22 and 26. Enclosure 28 is sufficiently filled with a radiopaque pliable material 30 so as to block a predefined amount of radiation from passing through enclosure 26, while allowing radiation to pass through aperture 24. One or more actuators 32 are operatively attached to one or more points of inner border 22. Actuators 32 are operable to deform the inner border 22 so as to modify a shape of aperture 24. For example, actuator 32 may be a solenoid or linear actuator with a push-pull rod attached to the perimeter of inner border 22.

The radiopaque pliable material 30 may include a radiopaque liquid, gas, powder, paste or thixotropic material. For example, the radiopaque pliable material 30 may include a radiopaque liquid, such as but not limited to, perfluorooctylbromide, a mixture of perfluorooctylbromide with other fluorocarbon liquids, or other radiopaque liquids such as barium sulfate, or any combination thereof. The radiopaque pliable material 30 may include a radiopaque powder, paste or thixotropic material, such as but not limited to, lead, tin, tungsten, antimony, bismuth, bismuth oxide, or any mixture thereof, or a dispersion (e.g., suspension or emulsion) of powdered radiopaque material in a carrier. The radiopaque pliable material 30 may include a radiopaque gas, such as but not limited to, xenon or krypton. The radiopaque pliable material 30 may include any combination of all or some of the above.

A sensor 34 may be provided that senses a parameter related to irradiation, such as but not limited to, radiation dosage, position of patient, position of tumor, temperature of tumor, etc. Sensor 34 may be a position sensor, accelerometer, capacitance sensor, radiation dose sensor, temperature sensor, etc. Sensor(s) 34 may be in operative communication with the actuator(s) 32 which change the shape of aperture 24 in accordance with information sensed by sensor(s) 34.

The collimator 12 may further include apparatus 36 for determining position and shape of the aperture (e.g., a camera). Sensor(s) 34 and apparatus 36 may operate in a closed loop control with actuator(s) 32 for changing and monitoring the shape of aperture 24.

Collimator 12 may be mounted on a movable interface 38 (FIG. 1) (e.g., an XY table or a turntable and the like) attached to gantry 14 at the output of radiation source 18. The movable interface 38 is operable to receive target positional data (from sensors 34, actuators 32 or apparatus 36 or other controllers or sensors or combination thereof) and accordingly move collimator 12 (and the associated aperture 24) relative to the radiation source 18 (typically, in a plane generally perpendicular to radiation beam 20) so that the radiation beam 20 that passes through aperture 24 is generally oriented toward the target (statically and/or dynamically).

The scope of the present invention includes both combinations and subcombinations of the features described hereinabove as well as modifications and variations thereof which would occur to a person of skill in the art upon reading the foregoing description and which are not in the prior art.

What is claimed is:

1. For use with an irradiation system, a collimator comprising:
    an inner border whose inner perimeter defines an aperture;
    an outer border positioned outwards of said inner border, an enclosure being defined and bounded between said inner and outer borders, said enclosure being sufficiently filled with a radiopaque pliable material so as to block a predefined amount of radiation from passing through said enclosure, while allowing radiation to pass through said aperture; and
    at least one actuator attached to at least one point of said inner border operable to deform said inner border so as to modify a shape of said aperture; and
    apparatus for determining position and shape of said aperture, wherein said apparatus comprises a camera.

2. The collimator according to claim 1, wherein said radiopaque pliable material comprises a radiopaque liquid.

3. The collimator according to claim 1, wherein said radiopaque pliable material comprises a radiopaque powder.

4. The collimator according to claim 1, wherein said radiopaque pliable material comprises a dispersion of powdered radiopaque material in a carrier.

5. The collimator according to claim 1, wherein said radiopaque pliable material comprises a radiopaque gas.

6. The collimator according to claim 1, wherein said inner border is constructed of a flexible material.

7. The collimator according to claim 1, further comprising a sensor that senses a parameter related to irradiation, said sensor being in operative communication with said at least one actuator, wherein said at least one actuator changes the shape of said aperture in accordance with information sensed by said sensor.

8. An irradiation system comprising:
    a radiation source that emits a radiation beam; and
    a collimator that collimates the radiation beam, said collimator comprising an inner border whose inner perimeter defines an aperture; an outer border positioned outwards of said inner border, an enclosure being defined and bounded between said inner and outer borders, said enclosure being sufficiently filled with a radiopaque pliable material so as to block a predefined amount of radiation from passing through said enclosure, while allowing radiation to pass through said aperture; and at least one actuator attached to at least one point of said inner border operable to deform said inner border so as to modify a shape of said aperture.

9. The irradiation system according to claim 8, wherein said collimator is mounted on a movable interface at an output of said radiation source, said movable interface being operable to receive target positional data and accordingly move said collimator and said aperture relative to said radiation source.

* * * * *